US012605085B2

(12) United States Patent
Ragauskas et al.

(10) Patent No.: US 12,605,085 B2
(45) Date of Patent: Apr. 21, 2026

(54) METHOD AND APPARATUS FOR HUMAN BRAIN NEUROPROTECTION DURING SURGERY

(71) Applicant: Kaunas University of Technology, Kaunas (LT)

(72) Inventors: Arminas Ragauskas, Kaunas (LT); Vytautas Petkus, Kaunas (LT); Edvinas Chaleckas, Kaunas (LT)

(73) Assignee: Kaunas University of Technology, Kaunas (LT)

( * ) Notice: Subject to any disclaimer, the term of this patent is extended or adjusted under 35 U.S.C. 154(b) by 1087 days.

(21) Appl. No.: 17/683,943

(22) Filed: Mar. 1, 2022

(65) Prior Publication Data

US 2023/0109678 A1     Apr. 13, 2023

Related U.S. Application Data

(60) Provisional application No. 63/255,152, filed on Oct. 13, 2021.

(51) Int. Cl.
*A61B 5/029* (2006.01)
*A61B 5/00* (2006.01)
(Continued)

(52) U.S. Cl.
CPC ............ *A61B 5/029* (2013.01); *A61B 5/0205* (2013.01); *A61B 5/031* (2013.01); *A61B 5/6814* (2013.01);
(Continued)

(58) Field of Classification Search
CPC ....... A61B 5/029; A61B 5/0205; A61B 5/031;

A61B 5/6814; A61B 5/7246; A61B 8/04; A61B 8/06; A61B 5/0053; A61B 5/4064; A61B 5/4836; A61B 5/746; A61B 5/0261; A61B 2505/05; A61B 5/026;
(Continued)

(56) References Cited

U.S. PATENT DOCUMENTS 9,474,451 B2     10/2016  Brady et al.
2002/0095087 A1*  7/2002  Mourad ............... A61B 8/0816
600/442
(Continued)

OTHER PUBLICATIONS

Dennis D. Doblar, PhD, MD. Cerebrovascular Assessment of the High-Risk Patient: The Role of Transcranial Doppler Ultrasound. Journal of Cardiothoracic and Vascular Anesthesia, vol. 10, No. 1 (Janaury) 1996 pp. 3-14.
(Continued)

*Primary Examiner* — Susan S Su
*Assistant Examiner* — Erin A Kim
(74) *Attorney, Agent, or Firm* — Harris Beach Murtha Cullina, PLLC

(57) ABSTRACT

The present invention is directed generally to a method and apparatus for human brain neuroprotection during surgery. The invention includes use of a heart-lung machine to generate periodic rectangular pulsation of blood flow. The invention uses a non-invasive CA monitor to continuously record transient functions such as dynamic autoregulation functions of a human brain cerebrovascular autoregulation system and process the data to generate an alarm to indicate CA impairment and take steps to minimize the CA impairment event.

16 Claims, 10 Drawing Sheets

(51) Int. Cl.

| | |
|---|---|
| *A61B 5/0205* | (2006.01) |
| *A61B 5/03* | (2006.01) |
| *A61B 8/04* | (2006.01) |
| *A61B 8/06* | (2006.01) |

(52) U.S. Cl.
CPC .............. *A61B 5/7246* (2013.01); *A61B 8/04* (2013.01); *A61B 8/06* (2013.01)

(58) Field of Classification Search
CPC ............ A61M 2230/10; A61M 1/3639; A61M 1/3666; A61M 60/113; A61M 60/216; A61M 60/38; A61M 60/515; A61M 60/562
See application file for complete search history.

(56) References Cited

U.S. PATENT DOCUMENTS

| | | | |
|---|---|---|---|
| 2010/0010322 A1 | 1/2010 | Brady | |
| 2012/0253211 A1* | 10/2012 | Brady | A61B 5/02028 604/6.11 |
| 2017/0119950 A1* | 5/2017 | Gilbert | A61M 1/3672 |
| 2020/0187866 A1 | 6/2020 | Antunes et al. | |

OTHER PUBLICATIONS

Danielle Greaves, Peter J. Psaltis, Daniel H. J. Davis, Tyler J. Ross, Erica S. Ghezzi, Amit Lampit, Ashleigh E. Smith, Hannah A. D. Keage. Risk Factors for Delirium and Cognitive Decline Following Coronary Artery Bypass Grafting Surgery: A Systematic Review and Meta-Analysis. J Am Heart Assoc. 2020;9(22):e017275.

Charles H. Brown IV, Karin J. Neufeld, Jing Tian, et al. Effect of Targeting Mean Arterial Pressure During Cardiopulmonary Bypass by Monitoring Cerebral Autoregulation on Postsurgical Delirium Among Older Patients. A Nested Randomized Clinical Trial. JAMA Surg. 2019;154(9):819-826.

Charles W. Hogue, Charles H. Brown IV, Daijiro Hori, Masa Ono, Yohei Nomura, Lauren C. Balmert, Nina Srdanovic, Jordan Grafman, Kenneth Brady, The Cerebral Autoregulation Study Group. Personalized Blood Pressure Management During Cardiac Surgery With Cerebral Autoregulation Monitoring: A Randomized Trial. Semin Thorac Cardiovasc Surg. 2021;33(2):429-438.

Birute Kumpaitiene, Milda Svagzdiene, Edmundas Sirvinskas, Virginija Adomaitiene, Vytautas Petkus, Rolandas Zakelis, Solventa Krakauskaite, Romanas Chomskis, Arminas Ragauskas, Rimantas Benetis. Cerebrovascular autoregulation impairments during cardiac surgery with cardiopulmonary bypass are related to postoperative cognitive deterioration: prospective observational study. Minerva Anestesiol. 2019;85(6):594-603.

Jurgen Ahr Claassen, Aisha Ss Meel-Van Den Abeelen, David M Simpson, Ronney B Panerai, and on behalf of the international Cerebral Autoregulation Research Network (CARNet). Transfer function analysis of dynamic cerebral autoregulation: A white paper from the International Cerebral Autoregulation Research Network. J Cereb Blood Flow Metab. 2016; 36(4): 665-680.

Stephan Strebel, Arthur Lam, Basil Matta, Teresa S. Mayberg, Rune Aaslid, David W. Newell. Dynamic and Static Cerebral Autoregulation during Isoflurane, Desflurane, and Propofol Anesthesia. Anesthesiology. 1995;83(1):66-76.

Yasin Hamarat, Mantas Deimantavicius, Vilius Dambrauskas, Vaidas Labunskas, Vilma Putnynaite, Paulius Lucinskas, Lina Siaudvytyte, Evelina Simiene, Akvile Stoskuviene, Ingrida Januleviciene, Vytautas Petkus, and Arminas Ragauskas, Prospective Pilot Clinical Study of Noninvasive Cerebrovascular Autoregulation Monitoring in Open-Angle Glaucoma Patients and Healthy Subjects, tvst. arvojournals. org | ISSN: 2164-2591: 1-10.

* cited by examiner a)

b)

c)

d)

METHOD AND APPARATUS FOR HUMAN BRAIN NEUROPROTECTION DURING SURGERY

CROSS REFERENCE TO RELATED APPLICATION

The instant application is a non-provisional application of and claims priority to U.S. Provisional Application No. 63/255,152, filed on Oct. 13, 2021, which is incorporated by reference in its entirety.

FIELD OF INVENTION

The present invention is directed generally to a method and apparatus for human brain neuroprotection during surgery.

BACKGROUND OF THE INVENTION

Cerebral blood flow (CBF) autoregulation means the maintenance of close to constant cerebral blood flow across a range of patient specific cerebral perfusion pressures (CPP). Autoregulation is a homeostatic mechanism which protects the brain from ischemic and hyperaemic injuries caused by too low or too high cerebral perfusion pressure for a specific individual patient. Real-time monitoring of the status of quasistatic ("static" in medical literature) cerebrovascular blood flow autoregulation (CA) is used in cardiac surgery, oncological surgery and organ transplantation surgery in order to identify time intervals of impaired CA and in order to minimize duration of such events that cause brain injuries. The inventors have discovered during a study of CA monitoring during cardiac surgery with cardiopulmonary bypass that the critical duration of the single longest CA impairment event which is associated with post-operative cognitive dysfunction (POCD) is approximately five minutes.

Existing non-invasive CA monitoring technologies (such as ultrasonic Transcranial Doppler, Ultrasonic Time of Flight based, or Near-infrared spectroscopy (NIRS) based technologies) which are based on arterial blood pressure (ABP) and cerebral blood flow velocity slow waves correlation and calculation of pressure reactivity index or other technologies which are based on ABP slow waves correlation with blood oxygenation slow waves are not a real-time technologies. They lack the ability to give instant real-time feedback. Such technologies need moving time averaging of recorded data in order to get a needed signal to noise ratio to enable a CA index calculation. In the prior art, the averaging time that is required to calculate moving time averages is close to or even more than five minutes. In order to identify, in real-time, a start point of a single longest CA impairment event what is needed and is necessary is a novel technology having a shorter time period with much higher time resolution. A time resolution which is much less than one minute is needed. In the prior art, slow ABP and intracranial pressure or intracranial blood volume, or blood oxygenation wave correlation or phase shift monitoring technologies cannot be used for real-time sub-minute temporal resolution of CA status monitoring.

An additional problem with existing prior art non-invasive CA monitoring technologies is the need to use non-invasive monitoring of ABP slow waves. Such monitoring is a source of signal noises and artifacts.

The invention is a novel technological solution which eliminates need to use ABP slow wave monitoring and which guarantees real-time sub-minute temporal resolution to identify a starting point to each single CA impairment event and monitoring with improved signal to noise ratio. Because the human brain CA system is nonlinear the one embodiment of the invention monitors the positive and negative transient functions of CA system in order to reflect the nonlinear dynamics of the CA system. The inventive apparatus provides the ability to reduce probability of a POCD event by elimination of ischemic and hyperaemic brain injuries to an individual patient.

BRIEF SUMMARY OF THE INVENTION

Generally, the invention provides a novel solution for human brain neuroprotection during surgery. The invention provides a novel rectangular mode of blood flow generated by a heart-lung machine, the ability to identify transient functions of the cerebral autoregulation system periodically with a sub-minute period and the ability to identify a starting point in time of a CA impairment event with a sub-minute temporal resolution The invention can include feedback from a CA status monitor to the cardiac surgery theater by an immediate alarm after identification of the start of a CA impairment event. The alarm gives a warning triggering active steps by the caregiver or surgeon to takes steps for neuroprotection of patient's brain from post-operative cognitive disfunction (POCD). In the preferred embodiment triggered alarm gives at least four minutes of time for cardiac surgeons and/or anesthetists to reestablish the patient's CA to an intact state by precise management of arterial blood pressure of individual patient.

Specific features of one embodiment of the invention includes a control sub-system of a heart-lung machine (pump) that generates control signals in order to generate periodic rectangular pulsation of blood flow produced by the heart-lung machine. The period of the rectangular pulsation is preferably less than one minute, and preferably more than seven seconds. During surgery, a non-invasive CA monitor (e.g. Transcranial Doppler, Ultrasonic Time of Flight, NIRS, etc) continuously records transient functions (dynamic autoregulation functions) of a human brain cerebrovascular autoregulation system. Because the human brain CA system is nonlinear an advantage of the invention is that for the first time once is able to monitor the positive and negative transient functions of CA system in order to reflect nonlinear dynamics of CA system. Another advantage of the invention is that the specific positive and negative monitoring of the transient functions from each rectangular ABP(t) pulse doubles the temporal resolution used for identification of the start time point for a CA impairment event. Monitoring those transient functions in real-time with sub-minute temporal is new and an improvement over prior art devices and systems.

According to the invention, the CA transient functions monitoring data are processed in order to identify a starting point of a single CA impairment event and to generate an alarm. The alarm creates neuroprotective feedback between CA monitor and surgical team including anesthetists and surgeons. When monitoring the patient the alarm is triggered when the predetermined correlation threshold is met. According to one embodiment of the invention the correlation factor of $R=0.8$ can be used as a threshold trigger. During monitoring, if the correlation factor is equal to or greater than 0.8 the alarm indicating CA impairment is triggered. When the correlation factor R is equal or more than 0.8 the probability of a false or wrong alarm indication of CA impairment is less than 0.05%.

Neuroprotection in this case means regulation of parameters of mean blood flow generated by the heart-lung machine and also regulation of anesthesia process in order to make duration of single CA impairment events shorter than five minutes minimizing the probability of a patient suffering POCD.

The invention includes a system and apparatus for human brain neuroprotection during surgery comprising a heart-lung machine with a pump that generates control signals in order to generate periodic rectangular pulsation of blood flow produced by heart-lung machine. The period of such rectangular pulsation is preferably less than one minute, but more than seven seconds. A non-invasive CA monitor (Transcranial Doppler, Ultrasonic Time of Flight, NIRS, etc) continuously records the transient functions (dynamic autoregulation functions) of a human brain cerebrovascular autoregulation system and includes a monitoring of positive and negative transient functions of the CA system in order to reflect the nonlinear dynamics of a patient's CA system. The CA transient functions monitoring data are processed in order to identify a start point of single CA impairment events and to generate an alarm which creates neuroprotective feedback between CA monitor and surgical team including anesthetists. In other embodiments, the alarm triggers a processor and software in the system to automatically adjust the heart-lung machine to adjust the regulation parameters of the heart-lung lung machine to minimize the impairment period. The regulation of parameters of mean blood flow generated by the heart-lung machine or regulation of anesthesia process can be modified in order to make duration of a single CA impairment events shorter than five minutes and to minimize a probability of POCD.

The invention also includes a method for human brain neuroprotection during surgery comprising generating with a heart-lung machine pump control signals in order to generate periodic rectangular pulsation of blood flow produced by heart-lung machine. The period of such rectangular pulsation is preferably less than one minute, but preferably more than seven seconds.

4 patient's blood flow velocities in the left and right middle cerebral arteries (MCA) according to an embodiment of the present invention.

Figure 8:
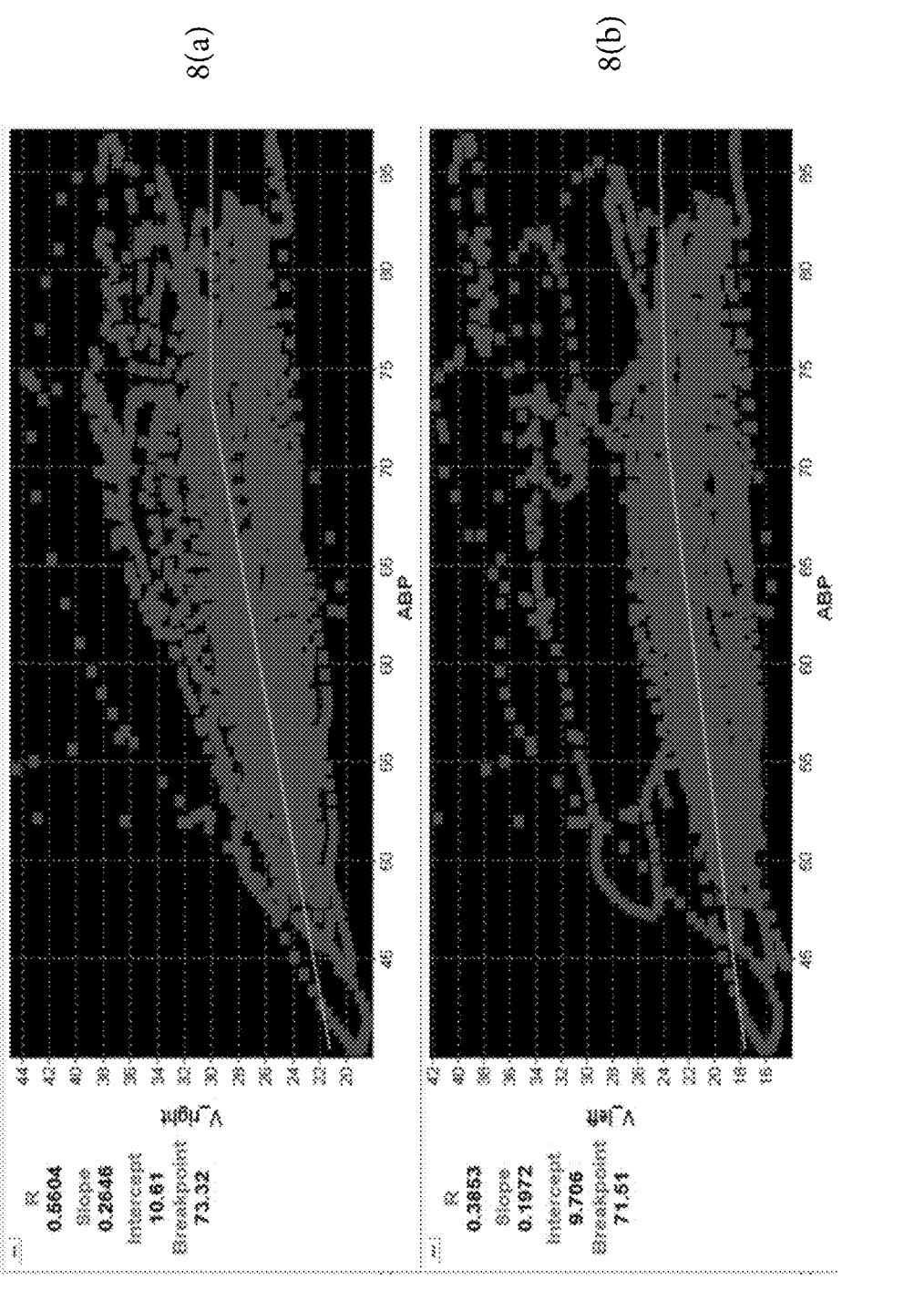

FIG. 8. Is a chart with graphs showing a surgery patient's ABP velocities in the right and left middle cerebral arteries (MCA) according to an embodiment of the present invention.

Figure 9:
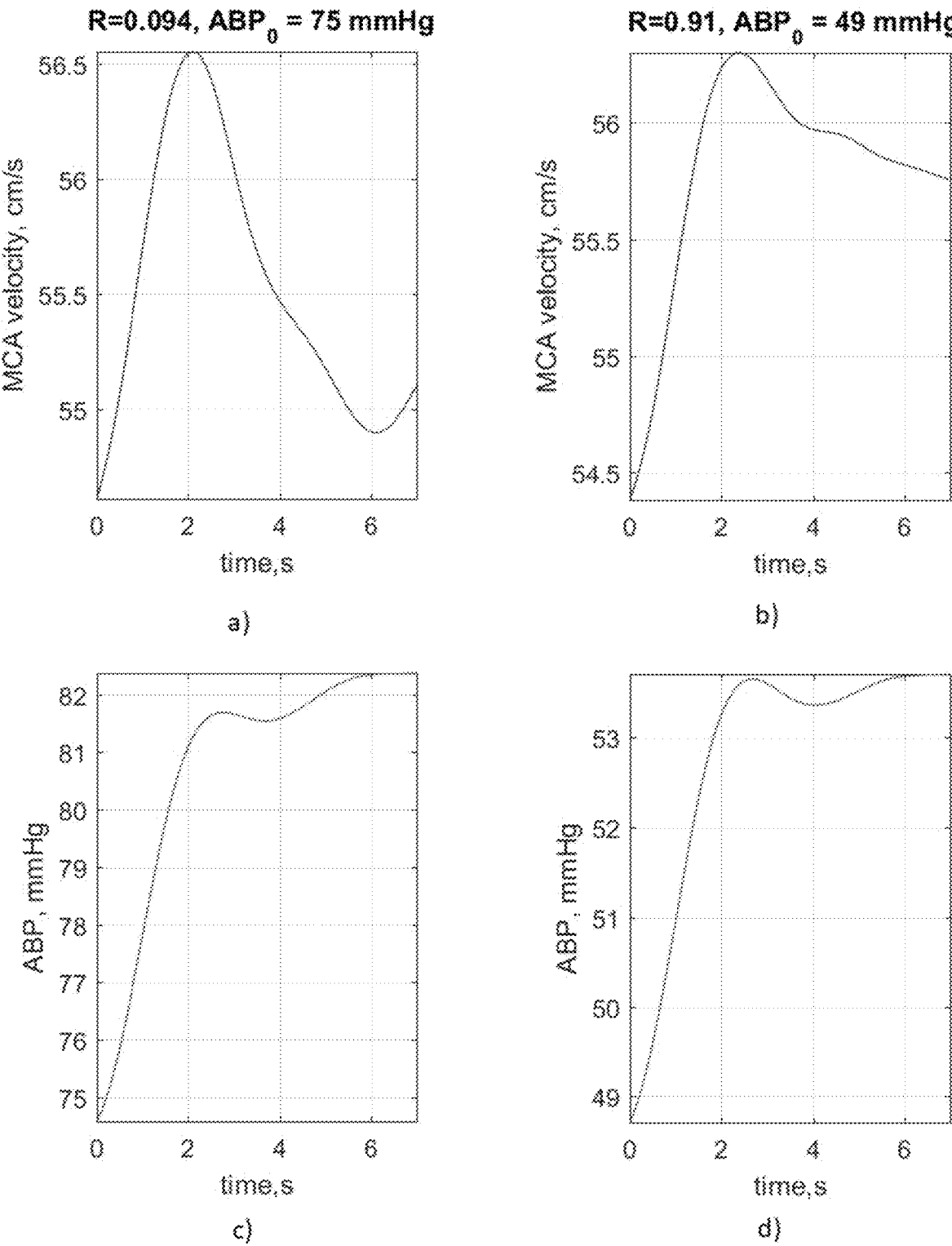

FIG. 9 Is a chart showing the Transient functions (TF) of CA represented as MCA blood flow velocity reactions to ABP(t) positive step functions according to an embodiment of the present invention.

Figure 10:
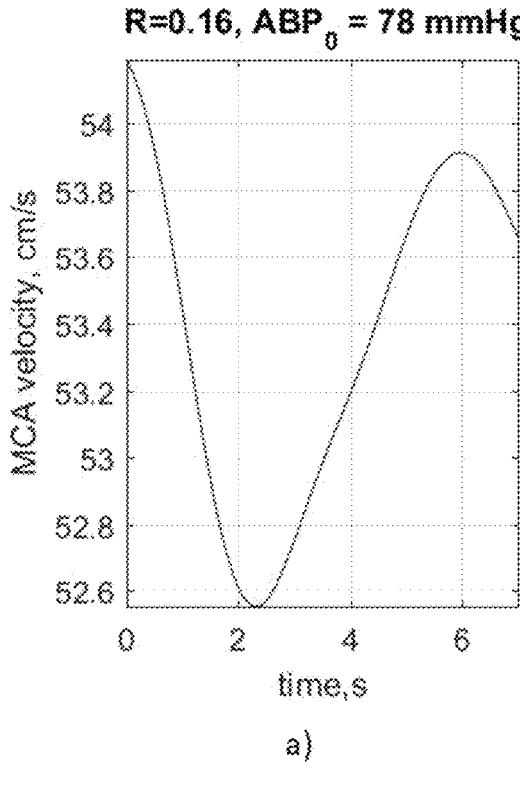
Figure 10:
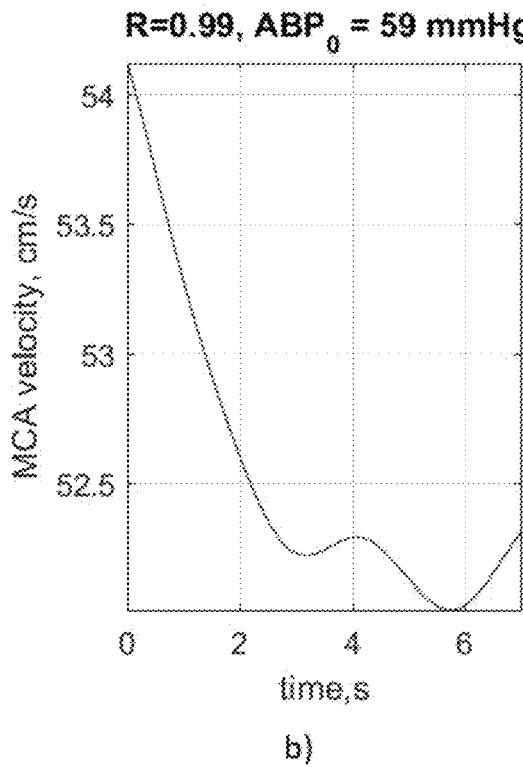
Figure 10:
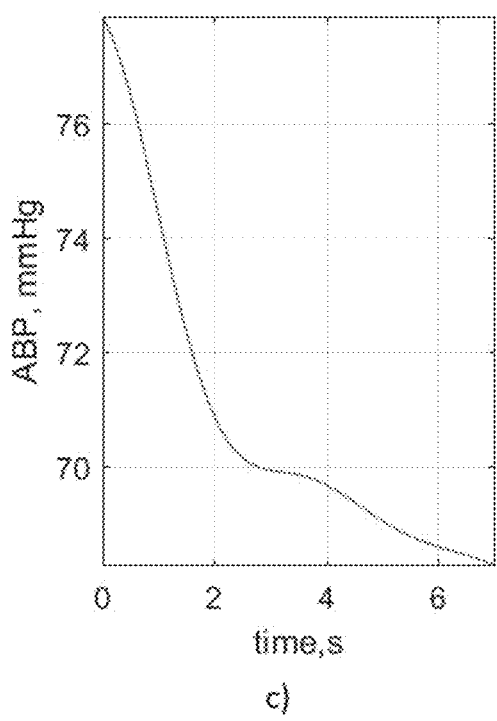
Figure 10:
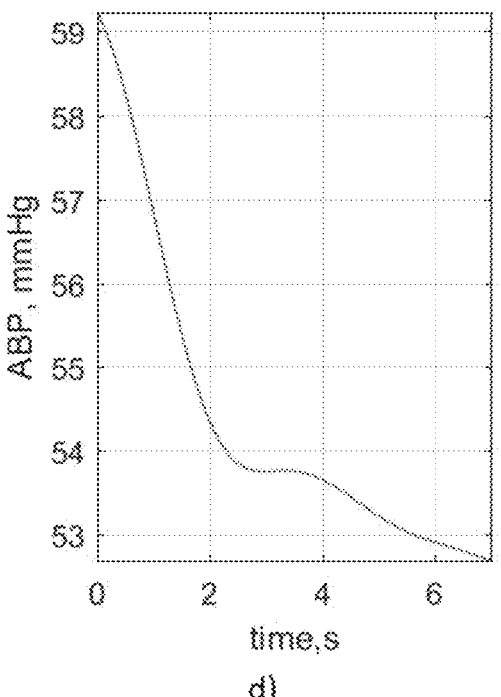

FIG. 10. Is a chart showing the Transient functions (TF) of CA represented a MCA blood flow velocity reactions to ABP(t) negative step functions according to an embodiment of the present invention.

DETAILED DESCRIPTION OF THE
INVENTION

The invention is based on a novel heart-lung machine blood flow formation mode using a periodic rectangular blood flow formation and monitoring of transient functions (dynamic autoregulation) of the human brain CA of a patient during surgery. A control subsystem of the heart-lung machine generates control signals in order to generate periodic rectangular pulsation of blood flow produced by heart-lung machine. The period of such rectangular pulsation is preferably less than one minute, but preferably more than seven seconds.

According to the invention a non-invasive CA monitor (Transcranial Doppler, Ultrasonic Time of Flight, NIRS, etc) continuously records transient functions (dynamic autoregulation functions) of human brain cerebrovascular autoregulation system. Such transient functions reflect intact or impaired CA situation with temporal resolution of seconds, not minutes as in existing monitoring technologies in the prior art. As the human brain CA system is nonlinear, the invention uses monitoring of positive and negative transient functions of the CA system in order to reflect nonlinear dynamics of the patient's CA system.

The CA transient functions monitoring data are processed in order to identify a start point of single CA impairment events and to generate an alarm which creates neuroprotective feedback between CA monitor and surgical team including anesthetists. Neuroprotection in this case means regulation of parameters of mean blood flow generated by a heart-lung machine and also regulation of the anesthesia process in order to make duration single CA impairment event shorter than five minutes and to minimize a probability of POCD.

During surgery, a non-invasive CA monitor (Transcranial Doppler, Ultrasonic Time of Flight, etc) continuously records transient functions (dynamic autoregulation functions) of human brain cerebrovascular autoregulation system. Because the human brain CA system is nonlinear the novelty of the invention is for the first time to monitor the positive and negative transient functions of CA system in order to reflect nonlinear dynamics of CA system and to get a two times better temporal resolution of CA transient function monitoring by including positive and negative transient functions in real-time analysis. The CA transient functions monitoring data are processed in order to identify a start point of single CA impairment events and to generate an alarm which creates neuroprotective feedback between CA monitor and surgical team including anesthetists and surgeons. Neuroprotection in this case means regulation of parameters of mean blood flow generated by health and lung machine and also regulation of anesthesia process in order to make duration of single CA impairment events shorter than five minutes and to minimize a probability of POCD.

Figure 1:
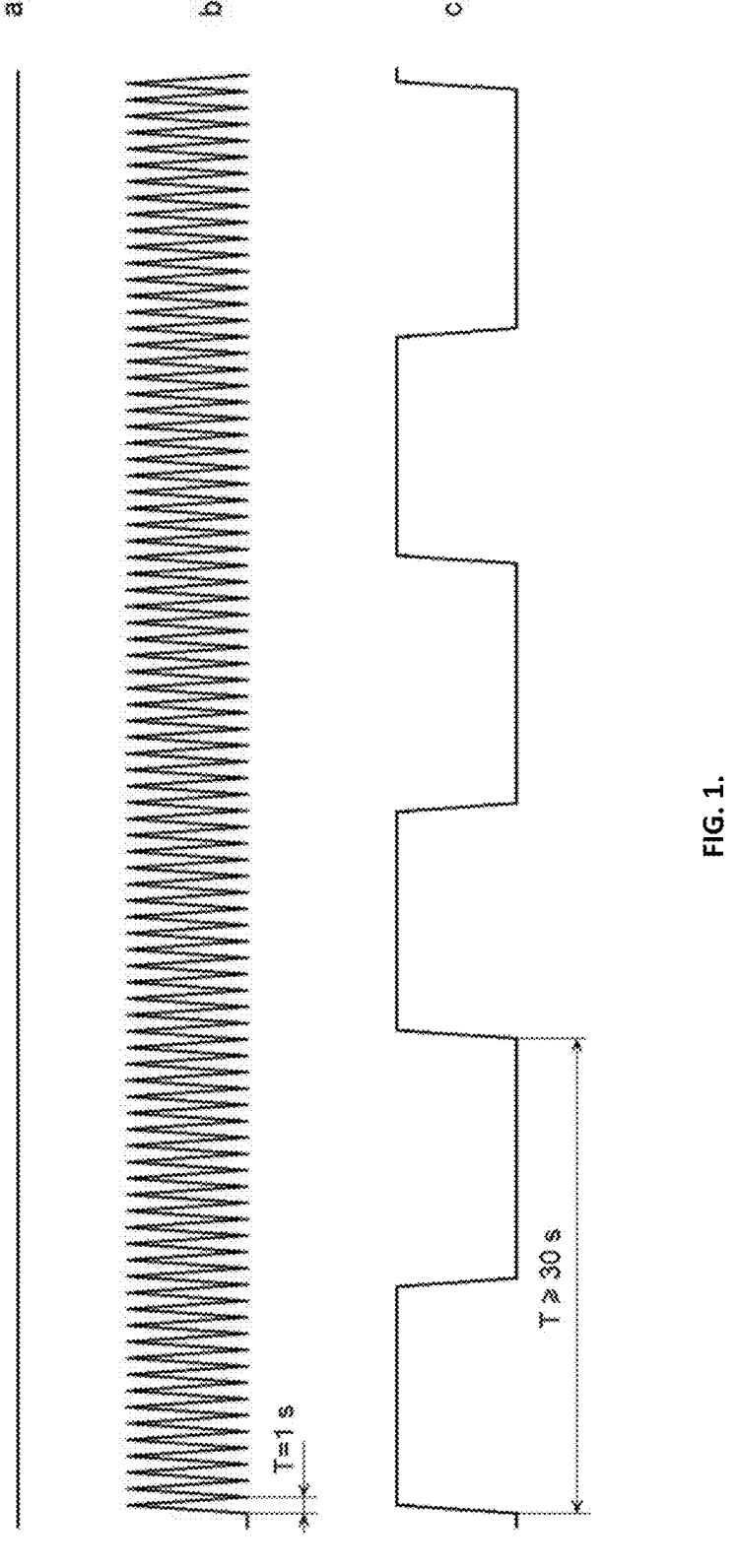
FIG. 1. Is a chart showing blood flow modes from the heart-lung machine of the periodic rectangular mode according to an embodiment of the present invention.

FIG. 1 shows the blood flow modes of a heart-lung machine including the use of the periodic rectangular mode. FIG. 1 shows two standard modes (a and b) of a heart-lung machine—constant flow mode (a) and heart pulsation imitating mode (b). It also shows a novel mode—rectangular pulsatile blood flow (c) which is needed in order to monitor the transfer functions of cerebrovascular autoregulation system. For the invention, the period (T) of rectangular pulses of blood flow need to be equal to or more than shortest physiological slow intracranial blood wave which is approximately 30 seconds. The patient's CA system has some inertia and a delay in reaction time. The reaction time of a healthy patient's CA system is close to seven seconds. Older patients have longer CA reaction times but their reaction time is typically not longer than 20-30 seconds.

Such a short period of rectangular blood flow pulses guarantees reliable recording of one positive and one negative transfer function of the cerebrovascular autoregulation system within a 30 second period. The possibility to receive diagnostic information on transient functions with subminute temporal resolution is needed in order to decide whether the patients' cerebrovascular autoregulation is intact or impaired as quickly as possible. If the patient's CA is impaired steps need to be taken immediately or correct the patients CA and organize and take steps for neuroprotection of the human brain cells which are dying within a few minutes without needed oxygen and glucose supplied by blood flow in cases of impaired cerebrovascular autoregulation. The fronts of rectangular blood flow pulses are a few hundred milliseconds in duration because of the dynamic characteristics of the heart-lung machine blood pump. The fronts, up to three seconds, of the "rectangular" blood and arterial blood pressure impulse of the heart-lung machine in FIG. 1 are longer than in real life because of pump vibrations and because of applied flow noise filtering procedures. Fronts of the "rectangular" blood flow and arterial blood pressure pulses have to be much shorter than the reaction time of patient's CA system (reaction time of young and healthy brain's CA system is approximately seven seconds) in order to generate a needed shape of ABP(t) function which needs to be close to a step function. The step function is needed in order to identify transient function of intact or impaired CA.

Figure 2:
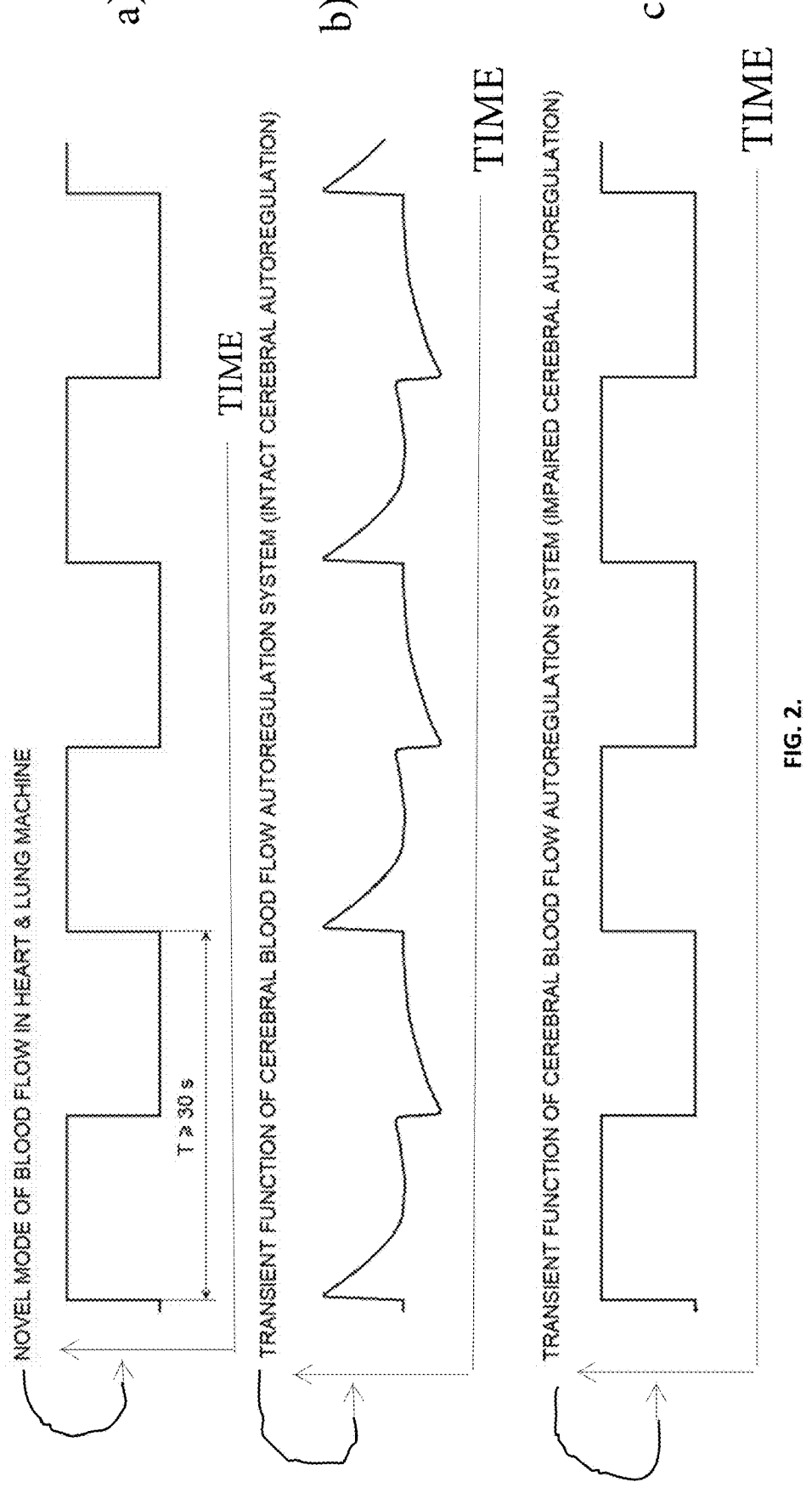
FIG. 2. Is a chart showing transient functions of a human brain CA system with positive and negative fronts of rectangular blood flow in cases of intact CA and impaired CA according to an embodiment of the present invention.

FIG. 2. Shows transient functions of a human brain CA system with positive and negative fronts of rectangular blood flow in cases of intact CA and impaired CA. FIG. 2(a) shows the novel mode of blood flow from the heart-lung machine. FIG. 2(b) shows transient functions of a cerebral blood flow autoregulation (cerebrovascular autoregulation) system reacting to positive and negative fronts of rectangular pulses of blood flow with an intact cerebral autoregulation system. FIG. 2(c) shows the transient function reacting to positive and negative fronts of rectangular blood flow with an impaired cerebral autoregulation system. In FIG. 2(b) transient functions in the case of intact cerebrovascular autoregulation are different in its reactions to positive and negative fronts of close to rectangular blood flow pulses because cerebral blood flow autoregulation system is nonlinear. In the cases of impaired cerebrovascular autoregulation systems the transient functions are similar to the shape of pulsatile blood flows shown in FIG. 2(c). When compared FIGS. 2(b) and 2(c) demonstrate the clear difference between transfer functions in cases of intact (FIG. 2(b)) and impaired (FIG. 2(c) cerebrovascular autoregulation system.

Figure 3:
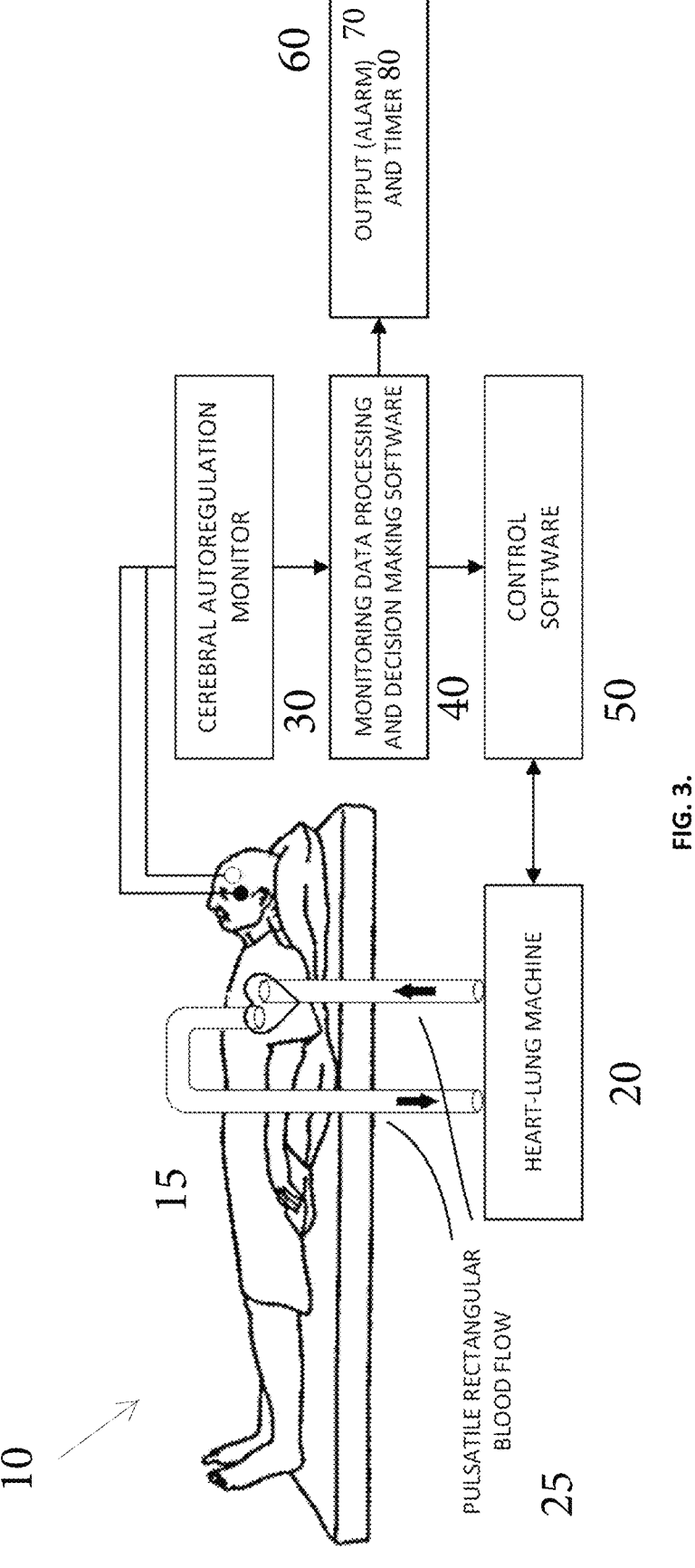
FIG. 3. Is a schematic showing the structure of one embodiment of an apparatus and system for human brain neuroprotection during surgery according to an embodiment of the present invention.

FIG. 3. Shows the structure of an embodiment of the present invention, a apparatus 10 that can be used on a patient 15 for human brain neuroprotection during surgery. FIG. 3 shows structural diagram of the apparatus and system including heart-lung machine 20 with rectangular pulsatile blood flow 25, cerebral autoregulation monitor 30 with needed temporal resolution in order not to distort recording of the shape of cerebrovascular autoregulation transfer function, monitor data processing and decision making software 40, control software 50 and alarm forming device 60 with an output or alarm 70 and a timer 80.

The alarm is triggered using a correlation factor for identification of similarity or differences between the ABP(t) step function and the recorded CA transient function. If the correlation factor shows similarity between the ABP(t) step function and the recorded transient CA function that is an indication that the patient's CA is impaired and the alarm is triggered. Such a correlation factor depends on a chosen set of metrics of similarity identification. The correlation factor R can be determined by several different embodiments and methodologies. Examples include use of Euclidian distance, difference of areas under curves or other metrics can be used in this case. The present inventive system knows when to trigger the alarm by monitoring of the correlation factor R and comparing it with a threshold number. The alarm starts immediately after identification of impaired CA triggered event (when R> threshold value). Experimentally identified threshold value in cardiac bypass surgery cases is R>0.8. Once the alarm is triggered the timer starts to show seconds and minutes of lasting CA impairment event in order to show to surgeons and anesthetists how many minutes they have for restoration of intact CA. Probability of POCD is minimal if restoration of intact CA is successful in less than 5 minutes. The timer stops when the patients CA is restored.

Non-invasive cerebral autoregulation monitor can be based on Transcranial Doppler or ultrasonic Time of Flight technologies or near infrared spectroscopy technologies or other technologies with needed sub-second temporal resolution.

Based on the output of the apparatus 10 decisions can be made to modify the mean arterial blood pressure or oxygen pressure in a heart-lung machine 20. For example, the operator of the heart-lung machine can adjust the mean ABP value. Also, the $CO_2$ and $O_2$ ratio to the patient can be adjusted with ABP to restore intact CA. The mean ABP can be managed in order to not cross the individual patient's specific CA lower (LLA) or upper limits (ULA) according to Lassen's cerebral autoregulation curve. The $CO_2$ and $O_2$ ratio can be managed during the anesthesia process in order to keep the mean ABP value within the patient specific CA LLA and ULA limits. In one embodiment an alarm is trigged to allow the surgeon, anesthesiologist or other care givers or decisions makers to make changes or adjustments to the system, such as changes in the anesthesia process in order to stop impairment of cerebrovascular autoregulation as soon as possible in real-time. Other adjustments can be made be made by a doctor or operator by changing the mean ABP value after being notified by the alarm. In order to restore impaired CA of an individual patient mean ABP is changed until it is close to or equal to the optimal mean ABP value somewhere between the patient specific lower limit of CA and upper limit of CA. Adjusting to optimal ABP ensures the best achievable intact CA for an individual patient, that is the transient function of CA show fully intact CA. The decisions to make adjustments and which adjustments to make can be made immediately by cardiac surgeons together with anesthetics or by means of artificial intelligence based decision making algorithms based on the immediate and timely warnings from the apparatus and system.

Figure 4:
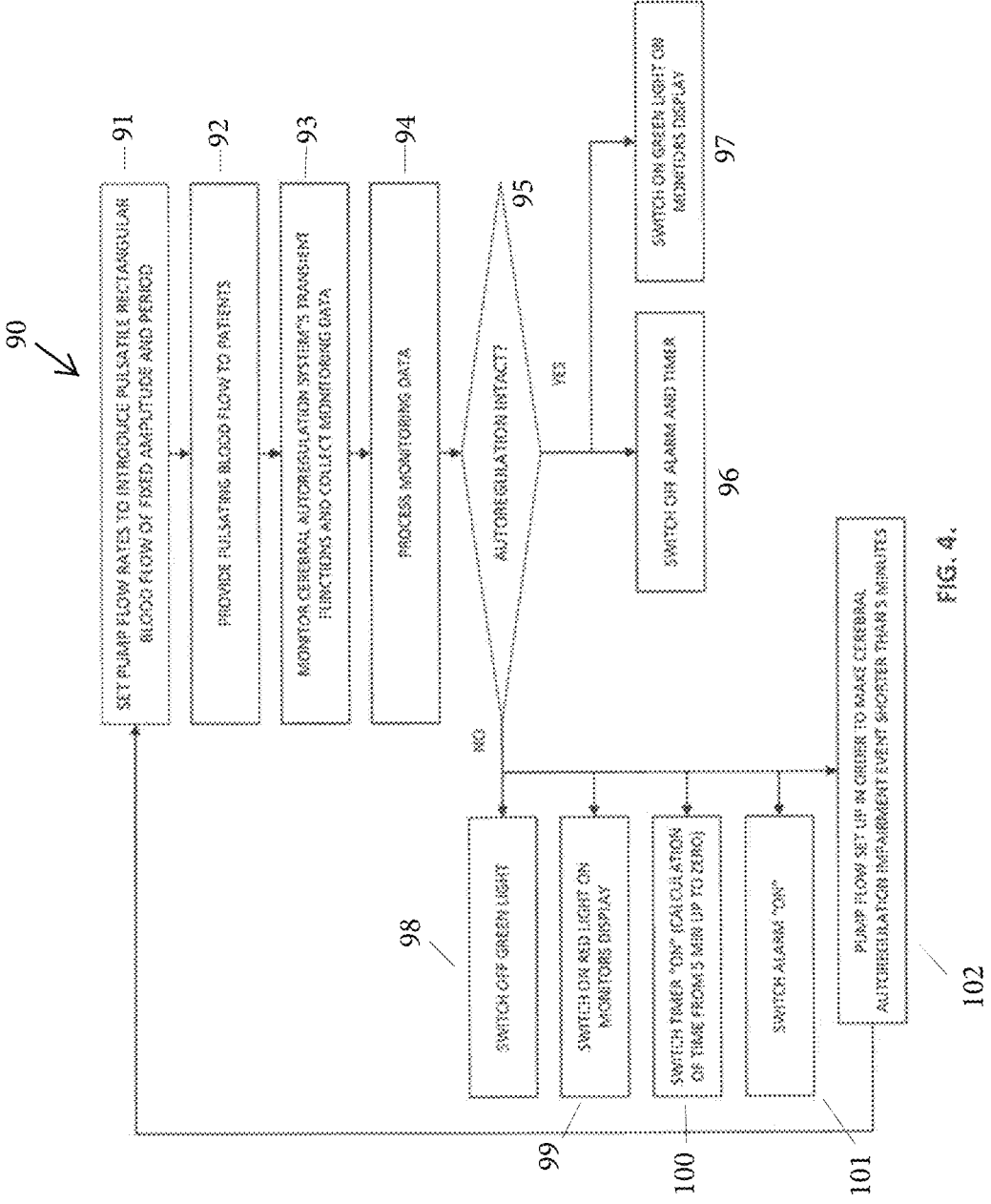
FIG. 4. Is a schematic showing the steps of a monitoring algorithm for CA monitoring and a data processing subsystem according to an embodiment of the present invention.

FIG. 4 is a schematic of an embodiment of the present invention showing the steps of a monitoring algorithm 90 for CA monitoring and a data processing subsystem. The first step is to set a heart-lung machine with blood pump flow rates to introduce a pulsatile rectangular blood flow of fixed amplitude and period 91. The pump is then activated to provide a pulsating blood flow to the patient 92. A noninvasive CA monitor such at as. transcranial Doppler, Ultrasonic Time of Flight, NIRS or other type of device can be used. The collected monitoring data is then processed 94. The data is processed and compared to a predetermined correlation factor to determine if the CA system of the patient is still intact. If the CA system of the patient is intact then the alarm and timer on the monitor are switched off 96. Optionally, a visual display such a green light on the monitor's display can be switched on 97 to indicate that the patient's CA system is operating properly. Alternatively, if after comparing the data to the predetermined correlation data the CA system of the patient is determined not to be intact then any visual display on the monitor, for example a green light, indicating the CA system of the patient is intact is immediately switched off, 98, and about the same time a different visual display on the monitor indicating the patient's CA system is not intact is switched on 99. A timer is then switched "on" (calculation of timer from 5 min up to zero) 100. An alarm is then switched "on" 101. This can be either an audio alarm, visual alarm, haptic alarm or any combination of the three. In one embodiment of the invention the operation of the pump flow of the heart-lung machine is then modified in order to make CA impairment event shorter than 5 minutes 102.

Figure 5:
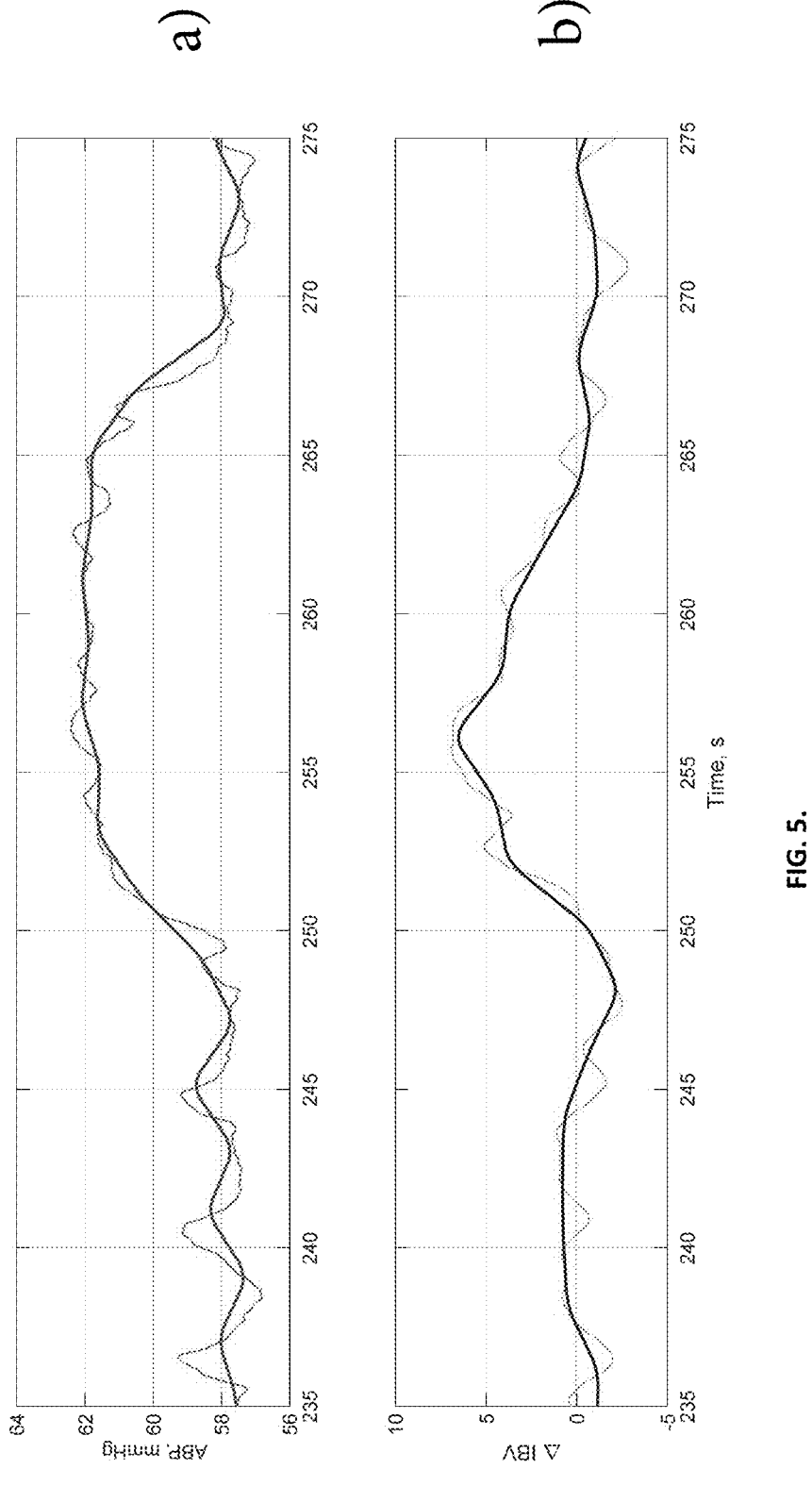
FIG. 5. Is a chart showing a surgery patient's arterial blood pressure and changes of the patient's intracranial blood volume according to an embodiment of the present invention.

According to one embodiment of the present invention FIG. 5(*a*) shows a non-invasively measured by ultrasonic time-of-flight technology reaction of a cardiac bypass surgery patient's intracranial blood volume (IBV) on an artificially induced blood flow impulse (a duration of approx. 15 seconds) in the heart-lung machine. The arterial blood pressure (ABP) impulse in FIG. 5(*a*) is a strongly correlated reaction to the blood flow impulse from the heart-lung machine and tracks the pulsatile rectangular blood flow from the heart-lung machine. In FIG. 5(*b*) reaction delta IBV (t) shows intact cerebrovascular autoregulation that does not track or correlate with the pulsatile rectangular blood flow of the heart-lung machine.

Figure 6:
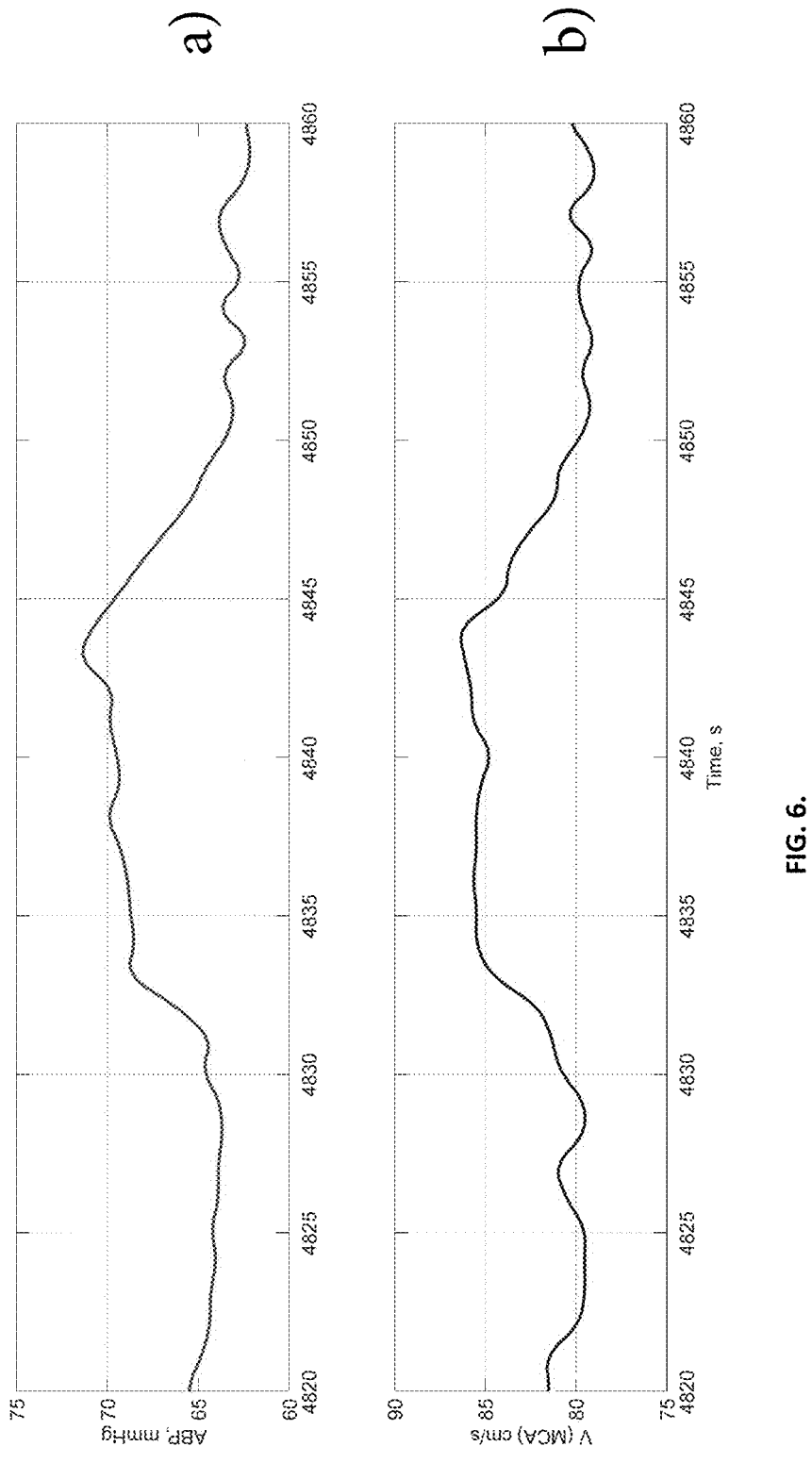
FIG. 6. Is a chart showing a surgery patient's arterial blood pressure and intracranial blood velocity according to an embodiment of the present invention.

According to an embodiment of the invention FIG. 6 shows the measured intracranial blood flow velocity (V(MCA)) in the middle cerebral artery (MCA) reaction of a cardiac bypass surgery patient on artificially induced blood flow impulse (duration approx. 15 seconds) in the heart-lung machine. Arterial blood pressure (ABP) impulse is strongly correlated reaction to blood flow impulse. In FIG. 6(*b*) reaction V (MCA) shows impaired cerebrovascular autoregulation because the V (CMA) tracks and correlates with the pulsatile rectangular blood flow of the hear lung machine.

Figure 7:
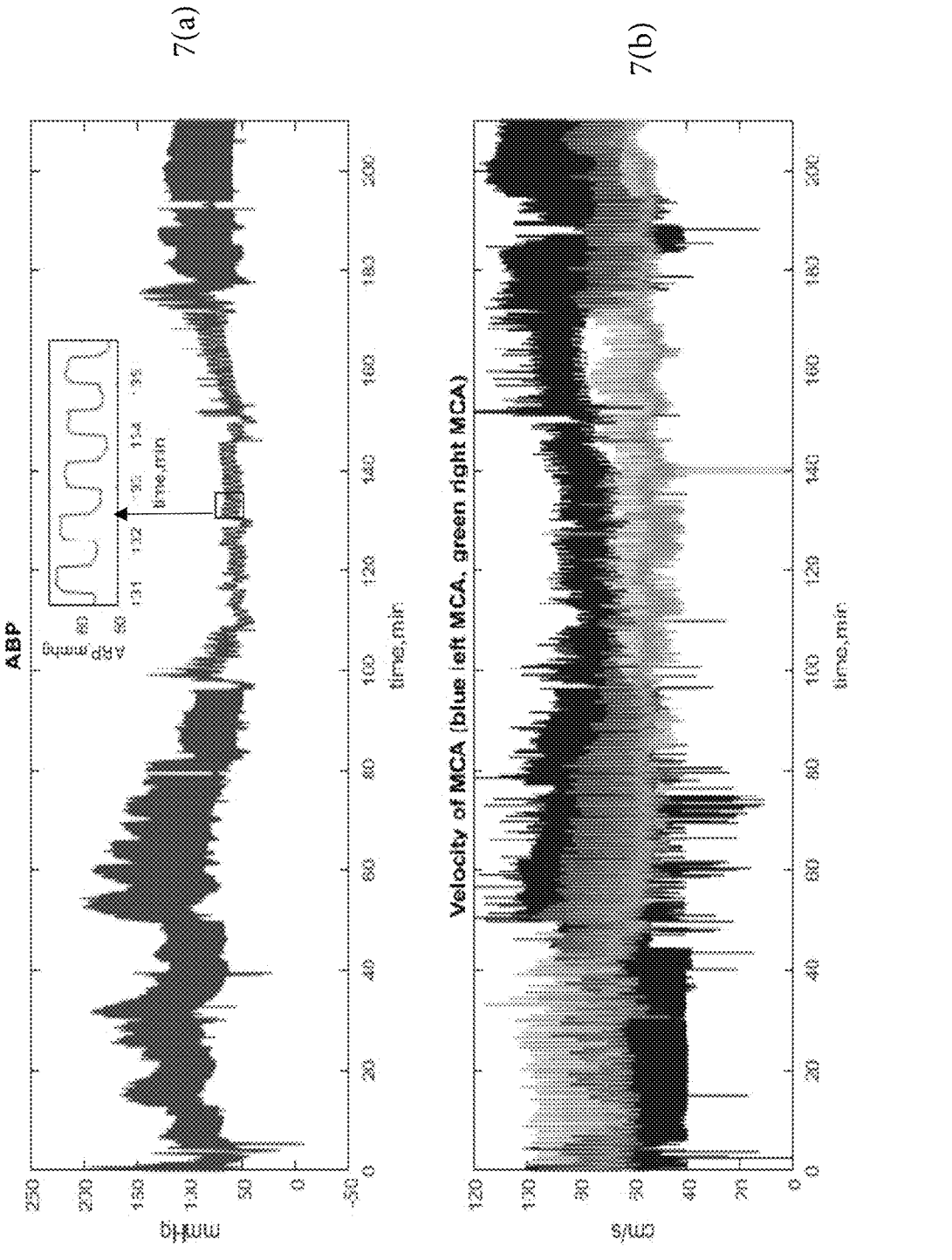
FIG. 7. Is a chart with a graph showing a surgery patient's ABP over time and a graph showing an example of a surgery

According to an embodiment of the invention FIG. 7 Shows raw data of time series monitoring during cardiac bypass surgery. The upper graph, FIG. 7(*a*) shows ABP(t)-arterial blood pressure versus time during a time extended surgery procedure. In this embodiment the heart-lung machine was operating from approximately the 98 minutes mark until approximately the 170 minute mark. The rectangular pulsation of ABP(t) (internal window inside an upper graph) is caused by rectangular pulses from modulate blood flow from heart-lung machine. The lower graph FIG. 7(*b*)

shows the transcranial Doppler monitoring raw data of blood flow velocities in the left and right middle cerebral arteries (MCA).

FIG. 8 shows the relationships between arterial blood pressure (ABP) and blood flow velocities in the right (V_right) and the left (V_left) middle cerebral arteries of cardiac bypass surgery patient. The green lines—Lassen cerebral autoregulation curves with breakpoints which represent the lower limits (LLA) of cerebral blood flow autoregulation at ABP=73.32 mmHg (upper graph) FIG. 8(*a*) and ABP=71.51 mmHg (lower graph) FIG. 8(*b*). The cerebral autoregulation is intact when the ABP values are above Lassen curve's breaking point and cerebral autoregulation is impaired when ABP values are below Lassen curve's breaking point.

It is presently impossible to identify individual patient specific lower (LLA) or upper (ULA) limits of CA in real-time. One embodiment of the invention uses comparison of ABP(t) step function and CA transient function shapes by correlation factor R (or other metrics) in order to confirm that unknown LLA or ULA is already crossed because of the wrong ABP management and the CA is impaired. The inventors found in previous clinical study of cardiac bypass surgery and POCD that a single longest CA impairment event with duration more than 5 minutes is highly correlated with POCD. The inventor's believe that management of ABP in order to restore intact CA within 5 minutes is an only way to avoid or minimize POCD in cardiac bypass surgery.

Unfortunately, identification of LLA position on ABP axis using existing technology is possible post factum only when ABP data are collected in wide ABP range (from 40 mmHg up to 90 mmHg in case shown in FIG. 8.). The invention solves this problem by identifying the LLA position almost in real-time using proposed transient function based CA classification factor TFx.

FIG. 9 shows the transient functions (TF) of CA represented as MCA blood flow velocity reactions (a) and (b) to ABP(t) positive step functions (c) and (d). "Positive" here means a first (rising) front of ABP(t) rectangular pulsation generated by heart-lung machine.

FIG. 9(*a*) shows intact CA and (b) shows impaired CA. Novel transient function based CA status identification index TFx is expressed as correlation index R between ABP(t) positive step functions and MCA blood flow velocity reactions.

R=0.094 when CA is intact (FIG. 9(*a*)) and when ABP0=75 mmHg e.g. ABP is above LLA.

R=0.91 when CA is impaired and when ABP0=49 mmHg (FIG. 9(*b*)), e.g. when ABP is below LLA.

Calculation of correlation factor R is used for simple evaluation of the differences between CA challenges (step functions of ABP(t) with positive and negative fronts) and CA reactions. When the CA transient function is similar in shape (high correlation) when compared to the ABP(t) step function that is an indication that CA is impaired. When the CA transient function is dissimilar in shape (low correlation) when compared with ABP(t) step function that is an indication that CA is intact. Not R only but all other metrics of two shapes similarity and difference (Euclidian distance, area under curve, etc.) can be used in this case. Threshold of R for alarm generation is close to 0.8 . . . 0.85.

Other metrics (Area under curve, Euclidian distance, etc.) could also be used with other versions of TFx definitions. In all cases TFx is able to classify CA statuses into "intact" and "impaired" almost in real-time independently from the applied metric.

FIG. 10. Transient functions (TF) of CA represented as MCA blood flow velocity reactions (a) and (b) to ABP(t) negative step functions (c) and (d). "Negative" here means second (falling) front of ABP(t) rectangular pulsation generated by heart-lung machine.

According to an embodiment of the invention FIG. 10(*a*) shows intact CA and FIG. 10(*b*) shows impaired CA. The transient function based CA status identification index TFx is expressed as correlation index R between ABP(t) negative step functions and MCA blood flow velocity reactions.

R=0.16 when CA is intact (FIG. 10(*a*)) and when ABP0=78 mmHg e.g. ABP is above LLA.

R=0.99 when CA is impaired and when ABP0=59 mmHg (FIG. 9(*b*)), e.g. when ABP is below LLA. Other metrics (Area under curve, Euclidian distance, etc.) could be used with other versions of TFx definitions. In all cases TFx (FIG. 9) and "negative" TFx (FIG. 10) are able to classify CA statuses into "intact" and "impaired" almost in real-time independently from applied metric. While correlation index R>0.8 index from a positive step function only can be used for identification of CA impairment start the preferred embodiment also uses the correlation from negative step function to assess CA impairment. Using positive and negative fronts of rectangular ABP(t) periodic pulsations in order improves temporal resolution of the invention by a factor of two when compared to a method using only one front.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teaching of the invention without departing from the essential scope thereof. Therefore, it is intended that the invention not be limited to the particular embodiments disclosed in the above detailed description, but that the invention will include all embodiments falling within the scope of the appended claims.

What is claimed is:

1. A system for human brain neuroprotection during surgery comprising a heart-lung machine that generates periodic rectangular pulsation of blood flow, the period of the rectangular pulsation of blood flow is less than one minute;

a non-invasive CA monitor for continuously recording data of the dynamic autoregulation functions of the human brain cerebrovascular autoregulation system and monitoring of positive and negative transient functions of the patient CA system in order to reflect nonlinear dynamics of the patient CA system;

a processor configured for processing the recorded CA transient functions data to identify a start point of a single CA impairment event and to generate an alarm;

wherein the heart-lung machine is configured to be adjusted after the alarm to regulate the parameters of mean blood flow generated by the heart-lung machine to minimize the duration of the single CA impairment event.

2. The system of claim 1 wherein the period of the rectangular blood flow is more than seven seconds.

3. The system of claim 1 wherein the non-invasive CA monitor is one of an ultrasound Transcranial Doppler device or ultrasound Time of Flight monitoring device or other non-invasive CA monitoring device with subsecond temporal resolution.

4. A system for human brain neuroprotection during surgery comprising a heart-lung machine that generates periodic rectangular pulsation of blood flow, the period of the rectangular pulsation of blood flow is less than one minute;

a non-invasive CA monitor for continuously recording data of the dynamic autoregulation functions of the human brain cerebrovascular autoregulation system and monitoring of positive and negative transient functions of the patient CA system in order to reflect nonlinear dynamics of the patient CA system;

a processor configured for processing the recorded CA transient functions data to identify a start point of a single CA impairment event and to generate an alarm;

wherein the heart-lung machine is configured to be adjusted after the alarm to regulate the parameters of mean blood flow generated by the heart-lung machine to minimize the duration of the single CA impairment event; and wherein the parameters of mean blood flow are regulated to reduce the CA impairment event to less than five minutes.

5. A system for human brain neuroprotection during surgery comprising a heart-lung machine that generates periodic rectangular pulsation of blood flow, the period of the rectangular pulsation of blood flow is less than one minute;

a non-invasive CA monitor for continuously recording data of the dynamic autoregulation functions of the human brain cerebrovascular autoregulation system and monitoring of positive and negative transient functions of the patient CA system in order to reflect nonlinear dynamics of the patient CA system;

a processor configured for processing the recorded CA transient functions data to identify a start point of a single CA impairment event and to generate an alarm;

wherein the heart-lung machine is configured to be adjusted after the alarm to regulate the parameters of mean blood flow generated by the heart-lung machine to minimize the duration of the single CA impairment event; and wherein the start point of the single CA impairment event is identified in real-time using a transient function CA factor.

6. The system of claim 5 wherein the transient function CA factor is the comparison of the MCA blood flow velocity transient function which reflects cerebral autoregulation transient function to an ABP(t) positive step function.

7. The system of claim 5 wherein the transient function of CA is a comparison of the MCA blood flow velocity transient function to an ABP(t) negative step function.

8. The system of claim 6 wherein a transient function based CA status identification index TFx is a correlation index R between ABP(t) positive step functions and MCA blood flow velocity reactions and when R is more than 0.8 the CA is impaired.

9. The system of claim 7 wherein a transient function based CA status identification index TFx is a correlation index R between the ABP(t) negative step functions and MCA blood flow velocity reactions and when R is greater than 0.8 the CA is impaired.

10. The system of claim 5 wherein a transient function based CA status identification index TFx is a correlation index R between ABP(t) functions and MCA blood flow velocity reactions.

11. The system of claim 4 wherein the start point of the single CA impairment event is identified in real time using a transient function CA factor.

12. The system of claim 11 wherein the transient function CA factor is the comparison of the MCA blood flow velocity transient function which reflects cerebral autoregulation transient function to an ABP(t) positive step function.

13. The system of claim 11 wherein the transient function of CA is a comparison of the MCA blood flow velocity transient function to an ABP(t) negative step function.

14. The system of claim 12 wherein a transient function based CA status identification index TFx is a correlation index R between ABP(t) positive step functions and MCA blood flow velocity reactions and when R is more than 0.8 the CA is impaired.

15. The system of claim 13 wherein a transient function based CA status identification index TFx is a correlation index R between the ABP(t) negative step functions and MCA blood flow velocity reactions and when R is greater than 0.8 the CA is impaired.

16. The system of claim 4 wherein a transient function based CA status identification index TFx is a correlation index R between ABP(t) functions and MCA blood flow velocity reactions.

* * * * *